(12) United States Patent
Kornberg et al.

(10) Patent No.: US 7,601,774 B2
(45) Date of Patent: *Oct. 13, 2009

(54) SYNTHESIS OF AROMATIC POLYHALOGENATED HALOMETHYL COMPOUNDS

(75) Inventors: Nurit Kornberg, Lehavim (IL); Michael Adda, Kfar Saba (IL); Michael Peled, Beer-Sheva (IL)

(73) Assignee: Bromine Compounds Ltd., Beer Sheva (IL)

( * ) Notice: Subject to any disclaimer, the term of this patent is extended or adjusted under 35 U.S.C. 154(b) by 266 days.

This patent is subject to a terminal disclaimer.

(21) Appl. No.: 11/632,788

(22) PCT Filed: Jul. 19, 2005

(86) PCT No.: PCT/IL2005/000768

§ 371 (c)(1),
(2), (4) Date: Mar. 12, 2007

(87) PCT Pub. No.: WO2006/008738

PCT Pub. Date: Jan. 26, 2006

(65) Prior Publication Data

US 2007/0205403 A1    Sep. 6, 2007

(30) Foreign Application Priority Data

Jul. 19, 2004    (IL) .................................. 163101

(51) Int. Cl.
C08K 5/03    (2006.01)
(52) U.S. Cl. ....................... 524/469; 570/254
(58) Field of Classification Search ......... 524/464–469; 570/254
See application file for complete search history.

(56) References Cited

U.S. PATENT DOCUMENTS

| | | | |
|---|---|---|---|
| 2,582,452 A * | 1/1952 | Olson et al. ................. | 524/114 |
| 3,874,155 A | 4/1975 | Knopka et al. | |
| 4,212,996 A | 7/1980 | Petersen et al. | |
| 5,811,470 A * | 9/1998 | Prindle et al. ................. | 521/85 |
| 5,821,393 A | 10/1998 | Millauer et al. | |
| 6,028,156 A | 2/2000 | Peled et al. | |
| 6,444,714 B1 * | 9/2002 | Gluck et al. ................... | 521/56 |
| 6,632,870 B2 | 10/2003 | Finberg et al. | |
| 2007/0257241 A1 * | 11/2007 | Kornberg et al. ............ | 252/601 |

FOREIGN PATENT DOCUMENTS

| | | |
|---|---|---|
| DE | 3828059 | 2/1990 |
| EP | 1 352 921 | 10/2003 |
| GB | 1 107 283 | 3/1968 |
| JP | 11279381 | 10/1999 |
| WO | WO 00/12593 | 3/2000 |
| WO | WO 03/064361 A * | 7/2003 |
| WO | WO 03/070685 A * | 7/2003 |
| WO | WO 2006/008738 A * | 1/2006 |
| WO | WO 2006/013554 A * | 2/2006 |

OTHER PUBLICATIONS

International Preliminary Report on Patentability of corresponding PCT application—8 pages.
Database WPI Section Ch, Week 199930 Derwent Pub. Ltd., GB; AN 1999-352814, XP002357473.
Database Ca Online, Chemical Abstracts Service, Ohio US; Dong, Shu'an et al: "One-pot synthesis . . . bromide" XP002357471.
Shishkin, S. et.al. In Zhurnal Organicheskoi Khimii (1981),17(6), 1270-5.
IL Application No. 163100; Bromine Compounds Ltd.; Jul. 19, 2004.

* cited by examiner

*Primary Examiner*—Peter Szekely
(74) *Attorney, Agent, or Firm*—Roach Brown McCarthy & Gruber, P.C.; Kevin D. McCarthy

(57) ABSTRACT

The present invention discloses a process for the preparation of highly pure pentabromobenzyl bromide, PBB-Br, wherein the benzylic bromination reaction is carried out in a suitable organic solvent in the presence of water and wherein the reaction temperature is such that it is sufficient to activate the initiator but not high enough to consume a substantial amount thereof.

13 Claims, No Drawings

SYNTHESIS OF AROMATIC POLYHALOGENATED HALOMETHYL COMPOUNDS

FIELD OF THE INVENTION

The present invention relates to the synthesis of aromatic polyhalogenated halomethyl compounds, particularly pentabromobenzyl bromide (PBB-Br).

BACKGROUND

Aromatic polyhalogenated halomethyl compounds are known as important building blocks for a variety of chemical products. These intermediate compounds have the advantage of good chemical reactivity and extremely high halogen content. Their major applications are in the production of flame retardants. Several processes for production of these intermediates are known in the literature.

For example a one pot synthesis using carbon tetrachloride as solvent and benzoyl peroxide as radical source was described by Dong S. et al. in Jingxi Huagong 14(3) (1997) 35-36. The yield of this process was 86% and the choice of the highly toxic solvent and the initiator are not easily applied on an industrial scale.

Another process was described by Shishkin, S. et. al. in Zhurnal Organicheskoi Khimii 17(6) (1981) 1270-5. Aromatic bromination of toluene was achieved using iron as catalyst, and the side chain bromination was done using either bromine with n-bromosuccinimide and benzoyl peroxide in carbon tetrachloride or with bromine in carbon tetrachloride using UV-irradiation at 80% to 86% yields.

DE 3,828,059 describes a process for side chain halogenation using a solvent and a catalyst such as nickel, cobalt, platinum or their salts.

U.S. Pat. No. 4,212,996 discloses a process for side chain chlorination of aromatic compounds completely halogenated in the nucleus and containing methyl groups. The process is a chlorination of side chains but the preparation of pure pentabromobenzyl bromide (PBB-Br) is also described. This was done in hexachlorobutadiene, HCBD, at 175° C.-185° C., using pentabromotoluene and bromine in the presence of 2,2'-azobis(isobutyronitrile).

In U.S. Pat. No. 6,028,156 a process for preparation of PBB-Br is described (Example 5). This process uses pentabromotoluene in chlorobenzene with bromine and 2,2'-azobis(isobutyronitrile) (AIBN). The process is actually a one-pot process for preparation of pentabromobenzyl acrylate (PBBMA) from pentabromotoluene (5BT) without isolating the PBB-Br.

Whether the final product is a flame retardant by itself or an intermediate for the production of the final flame retardant compound, the purity of these aromatic polyhalogenated halomethyl derivatives is a key issue.

In general the production of aromatic polyhalogenated halomethyl compounds involves two chemical stages: polyhalogenation of a methyl-aromatic compound and halogenation of the methyl group. The order of these two distinct chemical steps is one of the differences between known processes. If for example toluene is chosen as raw material, polybromination of the methyl-aromatic skeleton would result in pentabromotoluene. The pentabromotoluene is then chlorinated or brominated in the second chemical stage to produce pentabromobenzyl chloride or pentabromobenzyl bromide. On the other hand, toluene could be used to produce first the benzyl bromide or chloride necessary for the second stage of perbromination. Most known processes prefer to start with toluene and proceed via the pentahalotoluene to the pentahalobenzyl derivative.

The first chemical stage of aromatic perbromination is usually performed with the aid of a Lewis acid catalyst in a suitable, dry solvent. Such solvents are commonly dihalomethanes or their mixtures, dihaloethanes or their mixtures, and other solvents inert to bromine or chlorine in the presence of Lewis acid catalysts. Bromine itself can also be used as both the reagent and the solvent in such a process. The appropriate choice of the Lewis acid catalyst is also of high importance when the perbrominated product is intended to undergo another step of side chain bromination. Trace amounts of residual catalyst can strongly influence the side chain bromination as well as the color of the final product.

The second chemical stage, selective mono-halogenation of the methyl group, also known as benzylic halogenation, is achieved by a radical process, using some source of radical initiator to convert the bromine or chlorine molecule into reactive radicals that attack the methyl group to form the halomethyl functionality. The choice of radical source is rather limited for an industrial process, while the influence of this type of initiator on the final purity of the product is significant.

One of the most suitable radical initiators for this purpose is AIBN, 2,2'-azobisisobutyronitrile, CAS RN [78-67-1], 2,2'-azobis(2-methyl-proprionitrile).

The decomposition of AIBN is essential for the benzylic halogenation, side chain bromination, to proceed since the radicals formed by decomposition of AIBN initiate the formation of bromine radicals which are the active brominating species in this type of process. When elevated temperatures are applied, as described in prior art, the decomposition of AIBN is too fast, the major part of the radicals formed is consumed in side reactions of the methyl group or of the solvent. Therefore the inventors have found that it is highly recommended to perform such reactions at temperatures that will ensure high selectivity together with reasonable reaction time. At too low temperature the formation of radicals will be slowed down so that no effective reaction will occur.

The inventors have also found that the presence of an appropriate amount of water is essential for high efficiency of benzylic bromination. An equivalent amount of HBr is formed and must be efficiently removed in order to minimize the formation of $Br_3$. species which cannot give Br radicals upon encounter with AIBN radicals.

When two chemical stages are involved in the production of a new compound, it is always desirable, from the economic point of view, to perform both stages in the same pot without isolating the intermediate. On the other hand, it is difficult, in most cases, to obtain a product of high purity if the intermediate is not isolated and purified, since byproducts of the first stage also become involved in the chemistry of the second stage, increasing the range of impurities formed in the process. The process of the invention makes it possible to obtain a product of high purity even when the intermediate was not isolated and the process was performed in a one-pot manner.

The application of aromatic polyhalogenated halomethyl compounds as flame retardants or as intermediates for the production of other flame retardant compounds such as pentabromobenzyl acrylate (PBBMA) and polypentabromobenzyl acrylate (PBBPA) dictates the maximum allowed level of byproducts so that an optimal performance is achieved. For example, JP 11279381 (Application No. JP 98-85341) emphasizes the advantages of high purity polypentabromobenzyl acrylate containing no more than 1500 ppm of residual pentabromotoluene.

As will be appreciated by the skilled person, any flame retardant that is of higher purity, higher thermal stability and lower coloration, achieved by lower levels of foreign materials, will be more successful as a flame retardant than the same active ingredient with inferior properties.

PBB-Br has different uses, some of which may have less stringent quality requirements. However, the applicant hereof has found that in order to use PBB-Br as a flame retardant in polystyrene very specific conditions must be met in order to obtain high-quality products. The use of PBB-Br in foamed polystyrene is the subject of a separate patent application of the same applicant hereof (IL 163100, filed on Jul. 19, 2004).

The most important properties that should be fulfilled by a brominated organic compound, specially designed for flame retarding polystyrene articles, are:

1. Good uniform dispersion of the brominated additive in the polystyrene matrix. Such uniform dispersion is best achieved when the melting range of the brominated additive is lower than the typical processing temperature of the polystyrene, so that during processing the flame retardant additive is uniformly distributed throughout the polystyrene resin.

2. High thermal stability of the brominated organic flame retardant is another crucial property since additives of low thermal stability will limit the possibilities of regrinding and recycling the flame retarded material. Flame retardant additives of insufficient thermal stability will cause degradation of the polystyrene resin, by reducing the molecular weight of the styrene polymer foam and this in turn will immediately cause a drop in all mechanical and insulating properties of the foam, and even corrosion of the equipment in the most severe cases.

In principle there are several ways to ensure the necessary thermal stability of a chosen flame retardant molecule; among those the chemical purity of the compound directly influences its thermal stability.

It is a purpose of the present invention to provide an improved process that results in a product of high purity, suitable for use as an intermediate for the production of flame retardant agent or for direct application in polymeric resins as a flame retardant.

It is another purpose of the present invention to provide a process for production of aromatic polyhalogenated halomethyl compounds, especially pentabromobenzyl bromide, PBB-Br, of high quality as defined above, so that optimum performance is achieved when applied directly as a flame retardant in polymeric resins such as polystyrene or when used for the production of other flame retardant compounds such as PBBMA.

It is a further purpose of the present invention to provide a process for the production of PBB-Br that can be carried out either as a one-pot process or in two distinct chemical steps.

SUMMARY OF THE INVENTION

In one aspect the invention is directed to a process for the preparation of highly pure PBB-Br, wherein the benzylic bromination reaction is carried out in a suitable organic solvent in the presence of water and wherein the reaction temperature is such that it is sufficient to activate the initiator but not high enough to consume a substantial amount thereof. An illustrative reaction temperature is about 70° C.

In another aspect the invention is directed to the use of PBB-Br prepared according to the process of the invention, in the preparation of flame-retarded Expanded Polystyrene Foam (EPS) and to Expanded Polystyrene Foam comprising as a flame retardant an effective amount of said PBB-Br.

In a further aspect the invention relates to the use of PBB-Br prepared according to the invention, in the preparation of transparent, flame-retarded polystyrene, and to transparent, flame-retarded polystyrene, comprising as a flame retardant an effective amount of said PBB-Br.

In another aspect the present invention provides use of flame-retardant additives together with PBB-Br, which is prepared according to the invention, in the preparation of transparent, flame-retarded polystyrene.

In still another aspect the present invention provides transparent, flame-retarded polystyrene, comprising as a flame retardant an effective amount of said PBB-Br and other flame-retardant additives.

In still another aspect the invention is directed to a method for rendering flammable polystyrene flame retarded, to achieve UL94 V-2 rating, comprising adding to said polystyrene an FR-effective amount of PBB-Br. V-2 rated polystyrene comprising as a flame-retardant an effective amount of PBB-Br is also encompassed by the invention.

DETAILED DESCRIPTION OF THE INVENTION

Analytical Methods

Critical physical properties of pentabromobenzyl bromide and parameters for good performance of FR-polystyrene are measured by the following methods.

Methods for PBB-Br

Determination of melting point is performed using the BUCHI 545 instrument. A solid sample is introduced into a capillary tube after grinding into a fine powder. The start temperature is chosen to be 10° C. below the expected melting point with a heating rate of 1° C./min. The melting point determination is set to a threshold of 40% light transmission to the detector.

Melting point of PBB-Br can also be determined by Differential Scanning Calorimeter, DSC. DSC results were obtained with a Mettler-Toledo instrument model 821E. Samples were heated in aluminum crucibles, with a perforated lid, from room temperature to about 300° C. at 10° C./min under nitrogen, at 20 ml/min. For PBB-Br to be used in polystyrene a melting point higher than 183° C. measured in capillary or, a melt onset at 185° C. at least, as measured by DSC, is necessary.

Loss on drying is determined using a Halogen Moisture oven, HR 73, Mettler-Toledo. Residual solvent in PBB-Br suitable for application in polystyrene must be less than 1000 ppm.

Gas Chromatographic analysis—was performed on a Hewlett Packard mod. 5890 instrument, provided with a 15 m DB-1 column, 1μ, 0.53 mm OD. The flow was 2.5 ml/min Helium and the oven temperature was 230° C.-290° C. Residual byproducts, determined by Gas Chromatographic analysis, such as tribromotoluene, tetrabromotoluene and pentabromotoluene, should have a sum below 5000 ppm, with pentabromotoluene specifically less than 2000 ppm.

Iron content is determined by partially dissolving a sample in an organic solvent (immiscible with water) and the iron is extracted into HCl solution under reflux. The concentration of Iron is determined spectiophotometrically by complexation with phenantroline. High purity PBB-Br for application in polystyrene should contain less than 2 ppm of iron.

Thermal stability was determined by thermogravimetric analysis, TGA, for PBB-Br and for FR-PS including PBB-Br. Measurements were made using a Mettler-Toledo instrument model 850. 10 mg samples were heated in alumina crucibles from room temperature to about 600° C. at a heating rate of 10° C./min, under air at 50 ml/min.

Color determination—a 5 g sample of PBB-Br is dissolved in 60 ml of DBM. The color of the solution is determined by a comparator, Lovibond or LICO, and expressed in APHA values. Determination of color was performed on the LICO 200 instrument (DR LANGE). The analysis was performed using 11 mm or 50 mm tube (depending on the color values measured, according to the instruction manual, Operation Instruction, Ed 4, BDA 215).

Ionic bromide content was determined by dispersion of the sample in a mixture of water and methanol and titrating with $AgNO_3$. Ionic bromide content in PBB-Br suitable for polystyrene, and especially for Expanded Polystyrene Foam (EPS), was below 20 ppm Methods for FR-PS (Including PBB-Br)

HBr release from FR-PS—The amount of HBr released is measured by heating a weighed sample of FR-PS at 220° C. for 30 minutes. The HBr and/or HCl gas evolved are driven off the heated sample with nitrogen and trapped in water. The bromide and/or chloride ions are determined quantitatively by titration with $AgNO_3$.

Molecular weight distribution was measured by Gel Permeation Chromatography. The equipment used consisted of an HPLC pump (Merck-Hitachi model L6000), a UV detector (Jasco model UVIDEC-100-V) set at 254 nm, an automatic sampler (Micrometrics model 728 equipped with a six-port two-position Valco injection valve and 1 ml sample vials). The injection volume was 20 μL. Two sequentially connected Plgel 10 μm Mixed-B columns were used. The mobile phase was tetrahydrofuran, THF, at ambient temperature with a flow rate of 1 ml/min. Molecular weight distribution was calculated using an integrator (Spectra Physics model 4270) equipped with GPC Plus software module. Molecular weight distribution of FR-PS was compared with molecular weight distribution of non flame retarded PS.

Glass transition temperature was determined by DSC using a Mettler-Toledo instrument, model 821E. Samples were heated in aluminum crucibles, hermetically sealed lid, from room temperature to about 200° C. at 10° C./min under Nitrogen, at 20 ml/min. The value for the glass transition temperature was determined on the second run of a preheated sample, after annealing. Glass transition temperature of flame retarded PS was compared with glass transition temperature of non-FR polystyrene.

Flammability of FR-PS injection molded specimen was measured by UL-94V standard using a hood and burner as specified by UL.

Materials

Toluene reagent grade ex. Merck was dried on $CaCl_2$.
$AlCl_3$ reagent grade ex. Fluka was used as received.
Dichloromethane, DCM, was reagent grade ex. Merck.
Solvents, chlorobromomethane, CBM, and dibromomethane, DBM, were used as produced at Dead Sea Bromine Group, DSBG.

Bromine was used a's produced at Dead Sea Bromine Group, DSBG. 2,2'-Azobisisobutyronitrile, AIBN, ex AKZO.

Example 1

Perbromination of Toluene with Dibromomethane as Solvent

A 500 ml jacketed reactor provided with reflux condenser, thermowell, mechanical stirrer and toluene inlet, covered with heavy-duty aluminum foil against light penetration and connected to a heating cooling system was used. 150 ml of dry dibromomethane, DBM, 3.85 g, 0.0297 mole of aluminum chloride, $AlCl_3$, and 86 ml, 269.5 g, 1.684 mole, of bromine, $Br_2$' were introduced to the reactor. Temperature was set at 25° C. and 33.4 ml, 28.9 g, 0.314 mole, of toluene was fed via a peristaltic pump at a rate of 0.30 ml/min. The HBr generated was passed through two traps with DBM and a trap with solid $CaCl_2$ to an absorption column in which water was recycled by means of a centrifugal pump.

The conversion of toluene was followed-up by sampling the slurry of the reaction mixture, treating with water and sodium bisulphite solution, dissolving the solids in additional DBM and injecting the solution into a gas chromatograph. The reaction was almost finished when the feed of toluene was completed. A post reaction of one hour at 45° C.-65° C. brought the reaction to completion.

The pentabromotoluene, 5BT, content as determined by gas chromatograph was >99.5% and the sum of tribromotoluene, 3BT, all isomers, and tetrabromotoluene, 4BT, was less than 0.5%.

Work-up and isolation of 5BT was done by adding water and sodium bisulphite solution to the reaction mixture for catalyst destruction and reduction of excess free bromine. The aqueous layer was separated and the organic slurry was washed with water, neutralized and filtered. The crystalline product was further dried in a vacuum oven. The product obtained had a melting point of 288° C.-289° C.

Example 2

Perbromination of Toluene with Bromine as Solvent

A 500 ml jacketed reactor provided with a reflux condenser, thermowell, mechanical stirrer and toluene inlet, covered with heavy-duty aluminum foil against light penetration and connected to a heating cooling system was used. 175 ml, 544 g, 3.4 mole, of bromine and, 2.5 g, 0.019 mole of aluminum chloride, $AlCl_3$, were introduced to the reactor. Temperature was set at 30° C. and 30 ml, 25.95 g, 0.28 mole, of toluene was fed via a peristaltic pump at a rate of 0.09 ml/min. The HBr generated was passed through two traps with DBM and a trap with solid $CaCl_2$ to an absorption column in which water was recycled by means of a centrifugal pump. A post reaction of one and a half hours at reflux brought the reaction to completion. The conversion of toluene was followed-up by sampling the reaction mixture, treating with water and sodium bisulphite solution, dissolving the solids in DBM and injecting the solution into a gas chromatograph. When the sum of tribromotoluene, 3BT, all isomers, and tetrabromotoluene, 4BT, was less than 0.5% the reaction was stopped by addition of 300 ml of water and distillation of the excess bromine. After cooling to ambient temperature the residual bromine was reduced with 37% $NaHSO_3$ solution. The slurry was washed with water and neutralized with base. The product was analyzed by GC and contained less than 0.1% of tribromotoluene, 3BT, all isomers, and tetrabromotoluene, 4BT.

Example 3

Side Chain Bromination of Pentabromotoluene in Dibromomethane

A three necked run bottomed flask provided with stirrer, thermowell and reflux condenser was used. 62 ml of DBM, 46 g, 0.0946 mole of 5BT, produced as in example 1 or as in example 2, 26.8 g, 0.168 mole of $Br_2$ and 100 ml of water were introduced to the flask. The mixture was heated to 80° C. and 1.64 g azo-bis-isobutyronitrile, AIBN, was added. After one hour of reaction the conversion was complete, with less than 0.5% of 5BT, by gas chromatography. On cooling the pentabromobenzyl bromide, PBB-Br, crystallized as big very easily filterable crystals. The purity was 99.6% by gas chromatography.

Example 4

One-Pot Perbromination and Side Chain Bromination of Toluene in Dibromomethane A set-up similar to that described in the previous examples was used. 50 ml DBM, 2.6 g, 0.0195 mole, $AlCl_3$ and 109 g, 0.68 mole of bromine, $Br_2$ were fed to the reactor. This mixture was kept at 25° C.-35° C. while 8.74 g, 0.095 mole of toluene was fed via a peristaltic pump at a rate of 0.25 ml/min for 35 minutes. After one additional hour the reaction was completed, according to GC analysis, with less than 0.5% of 3BT+4BT. The catalyst was decomposed and washed out by the addition of 100 ml of water. The aqueous layer was removed and another 100 ml of water were added. The reaction mixture was heated to 80° C. and 1.64 g of AIBN was added. After two hours the reaction was completed, as determined by gas chromatography. The aqueous, acidic layer was removed, and another 100 ml of fresh water was used for washing. The organic layer was neutralized with base and the crystalline product, PBB-Br, was filtered and dried. The purity of this product was 99.6% by gas chromatography.

Example 5

One-Pot Perbromination and Side Chain Bromination of Toluene in Solvent Mixture A set-up similar to that described in the previous examples was used. 60 ml of a solvent mixture composed of 7% dichloromethane, DCM, 12% of chlorobromomethane, CBM, and 81% of DBM was fed to the reactor. The solvent was previously dried over silica gel to less than 250 ppm of water. 2.5 g, 0.019 mole of $AlCl_3$ powder was added. Then 137 g, 0.856 mole, bromine, $Br_2$ was added. Once all of the reagents had been charged, 14.4 g, 0.157 mole, of toluene feed was started at 25° C.-30° C. Toluene addition was completed within one hour. After an additional 30 minutes, a sample was taken for analysis by gas chromatography. Conversion was complete, with 0.15% of 3BT+4BT. The catalyst was deactivated by careful addition of 35 ml of water. When the exothermic reaction was completed, the acidic aqueous layer was removed by suction. The efficient removal of aluminum ions from the reaction mass was monitored by analysis for aluminum content in the organic reaction mixture, preferably less than 100 ppm. Another 35 ml of fresh water were added and immediately afterwards another 29 g, 0.181 mole of bromine, $Br_2$, was added and the mixture was heated to 70° C. 1.5 g of freshly prepared slurry of AIBN in 5 ml of water was added stepwise to the reaction mixture over three hours. Four hours after the addition of AIBN began; the reaction was completed, with less than 0.5% of 5BT. The reaction mixture was cooled to 40° C. and the residual free bromine was reduced by the addition of 37% $NaHSO_3$ solution. The aqueous acidic layer was removed and the reaction mixture was washed with another 30 ml of water. The organic reaction mixture was neutralized with 5% $NaHCO_3$ solution. Crystallization was completed by cooling to 15° C. and the product, PBB-Br, was filtered. The cake was washed with water and dried in a vacuum oven. The organic filtrate was separated and subjected to fractional distillation. The distillate was used for consecutive bromination experiments after determination of its composition by gas chromatography. The yield of PBB-Br was 93% by weight. The purity as determined by GC analysis was 99.7%, with less than 0.3% of 5BT and less than 0.1% residual solvents and water. Ionic bromide content was below 20 ppm, color was 15 APHA, melting range 183.5° C.-185° C. The thermal stability was measured by TGA: 1% weight loss at 208° C., 2% weight loss at 220° C., 5% weight loss at 238° C. and 10% weight loss at 253° C. The composition of the recovered distilled solvent for further use was 0.2% DCM, 9.3% CBM and 90.3% DBM with less than 0.07% of bromoisobutyronitrile, BIBN.

Example 6

Preparation of Injection Molded Polystyrene Specimen with PBB-Br and Other Flame Retardant Additives For the purpose of flammability measurement and analytical characterization of polystyrene flame retarded with PBB-Br and other common additives, injection molded specimens were prepared.

Flame retardancy of the injection molded and compression molded flame-retarded polystyrene specimens was tested according to the different test methods described in the following Table V.

Compounding

All the components (plastic pellets and powders) were weighted on Sartorius semi-analytical scales with consequent manual mixing in a plastic bag. Formulations were compounded in Berstorff twin-screw extruder Type ZE-25, L/D 32: 1 fed from one feeder. Compounding conditions are presented in Table I below. The obtained strands were cooled in a water bath and then pelletized in the Pelletizer 750/3 ex. Accrapak Systems Limited. The obtained pellets were dried in a circulating air oven at 70° C. for two hours.

Injection Molding

The compounded pellets were molded using Arburg-Allrounder machine model 320 s/500-150. LOI and UL test specimens were molded, mold no. S 22963 was used. Molding conditions are presented in Table II below.

TABLE I

Regime of compounding in co-rotating twin-screw extruder ex Berstorff

| Parameter | Units | Set Values |
|---|---|---|
| $T_1$ Feeding zone | ° C. | no heating |
| $T_2$ | ° C. | 140 |
| $T_3$ | ° C. | 150 |

TABLE I-continued

Regime of compounding in co-rotating
twin-screw extruder ex Berstorff

| Parameter | Units | Set Values |
| --- | --- | --- |
| $T_4$ | ° C. | 170 |
| $T_5$ | ° C. | 170 |
| $T_6$ | ° C. | 180 |
| $T_7$ vent | ° C. | 180 |
| $T_8$ | ° C. | 180 |
| $T_9$ nozzle | ° C. | 190 |
| Screw speed | RPM | 375 |
| Feeding rate | kg/hour | 11.8 |

TABLE II

Regime of injection-molding

| Parameter | Units | Values |
| --- | --- | --- |
| $T_1$ (Feeding zone) | ° C. | 160 |
| $T_2$ | ° C. | 180 |
| $T_3$ | ° C. | 180 |
| $T_4$ | ° C. | 180 |
| $T_5$ (nozzle) | ° C. | 180 |
| Mold temperature | ° C. | 40 |
| Injection pressure | Bar | 1700 |
| Holding pressure | Bar | 700 |
| Back pressure | Bar | 0 |
| Injection time | Sec | 0.1 |
| Holding time | Sec | 1.5 |
| Cooling time | Sec | 10 |
| Mold closing force | kN | 128 |
| Filling volume (portion) | Cc | 30 |
| Injection speed | cc/sec | 20 |

The flow promoter used in the following examples was commercial Interox C-C DFB Peroxide Chemie; 2,3-dimethyl-2,3-diphenyl butane, also referred to as dicumyl.

TPP (triphenyl phosphate), Reomol ex Ciba Geigy, was used as one commercial example for phosphate ester.

4,4'-biphenol phenylphosphate was used as one example of phosphate ester. The material is described in Patent Application EP 1 327 635.

Polystyrene-Flame Retardant Formulations 1-12, the properties of which are detailed in Table III, (In the Table Exp. No.=Formulation No.) were compounded and injection molded substantially according to the compounding and injection molding procedures disclosed above. Their regimes are detailed in Tables I and II, respectively.

Table III details the different formulations components used for injection-molded specimens 1-12. As can be seen, formulations contain PBB-Br in different relative amounts with or without the addition of phosphorous flame-retardant synergist and dicumyl flow-promoter with one formulation containing only polystyrene for reference.

Several properties of polystyrene flame retarded with PBB-Br are for all practical purpose identical to the properties of non-FR-Polystyrene.

Glass transition temperature of flame retarded PS, formulations 2&3, compared with glass transition temperature, Tg, of non-FR polystyrene, formulation 1, would indicate any changes in flowability of the polystyrene melt during compounding and extrusion as well as degradation or cross-linking of the polystyrene resin caused by the presence of the flame retardant agent. Practically there are no changes in Tg when high purity PBB-Br is used as flame retardant for polystyrene.

TGA results for neat polystyrene, formulation 1, and for polystyrene with PBB-Br, formulations 2&3 are practically identical, indicating that when high quality PBB-Br is used as flame retardant for polystyrene no adverse influence on thermal stability of the injected article was found. This would be a major advantage of such formulations when attempting recycling of the FR-PS compound.

Molecular weight distribution, Mw and Mn, for formulations 2&3 is the same as for non-FR polystyrene, formulation 1, indicating that when high purity PBB-Br is used in polystyrene, no damages occurred to the polystyrene resin because of the presence of the flame retardant agent during compounding and molding.

When flow promoter type additives, such as 2,3-dimethyl-2,3-diphenyl butane are used, see formulation 6, the Tg, which reflects flow properties of the polystyrene, is reduced, meaning improved flowability and higher throughput compared to the same formulation without flow promoter, formulation 3 for comparison.

The effect of both types of phosphate additives, TPP (triphenyl phosphate) and PFR-221, is also seen in the Tg of the polystyrene. Compare formulations 9&10 for the use of TPP and formulations 7&8 for the use of PFR-221 with formulation 3.

None of these additives in combination with high purity PBB-Br as flame retardant influenced the thermal stability as measured by coloration or by TGA or by HBr release.

Example 7

Preparation of Transparent Flame Retarded Injection Molded Polystyrene with PBB-Br Injection molded test specimens were prepared as described in Example 6. Flammability rating, color and transparency data for formulations 1 to 12 are detailed in Table IV.

The high efficiency of PBB-Br as flame retardant for crystalline, injection molded polystyrene is shown by the surprising UL-94 V-2 rating, achieved at very low bromine loading without any synergetic effect of antimony oxides. All formulations were colorless and transparent.

In order to appreciate the surprising result achieved by the invention, reference can be made to U.S. Pat. No. 6,632,870, which deals with transparent plastic materials that achieve V-2 rating using up to 40% FR loading. As can be seen, e.g., by looking at Table I (Example 1) of the patent, 15% of FR-1808 were needed to achieve V-2 rating.

TABLE III

Analytical data for Injection molded FR-PS test pieces

| Exp No./ Formulation No. | Br-FR type | % Br-FR | % Br in formulation calculated | P-FR type | % P-FR | % P in formulation calculated | % Dicumyl in formulation | Tg °C. | TGA 10° C./min 1% | 2% | 5% | 10% | HBr release ppm | Mw | Mn |
|---|---|---|---|---|---|---|---|---|---|---|---|---|---|---|---|
| 1 | — | — | — | — | — | — | — | 104.2 | 287 | 299 | 317 | 333 | — | 187000 | 66500 |
| 2 | PBB-Br | 2.5 | 2.0 | — | — | — | — | 105.6 | 273 | 291 | 319 | 337 | 178 (prepared by compression molding) | 184000 | 66000 |
| 3 | PBB-Br | 1.8 | 1.5 | — | — | — | — | 105.7 | 276 | 295 | 318 | 333 | 546 | 186000 | 71000 |
| 4 | PBB-Br | 1.2 | 1.0 | — | — | — | — | Not determined | | | | | | | |
| 5 | PBB-Br | 1.8 | 1.5 | — | — | — | 0.2 | Not determined | | | | | | | |
| 6 | PBB-Br | 1.8 | 1.5 | — | — | — | 0.4 | 102.4 | 267 | 284 | 306 | 324 | 476 | 191000 | 72500 |
| 7 | PBB-Br | 1.8 | 1.5 | PFR-221 | 1.5 | 0.143 | — | Not determined | | | | | | | |
| 8 | PBB-Br | 1.8 | 1.5 | PFR-221 | 3.0 | 0.285 | — | 99.3 | 275 | 293 | 320 | 339 | 449 | 195000 | 77000 |
| 9 | PBB-Br | 1.8 | 1.5 | TPP | 1.5 | 0.143 | — | Not determined | | | | | | | |
| 10 | PBB-Br | 1.8 | 1.5 | TPP | 3.0 | 0.285 | — | 97.2 | 257 | 276 | 308 | 325 | 488 | 195000 | 77000 |
| 11 | PBB-Br | 1.8 | 1.5 | TPP | 0.8 | 0.076 | 0.1 | 101.1 | 265 | 287 | 315 | 330 | 200 | 190000 | 67800 |
| 12 | PBB-Br | 1.8 | 1.5 | TPP | 1.5 | 0.143 | 0.2 | 97.5 | 261 | 280 | 309 | 327 | 760 | 190000 | 67700 |

\* PFR-221 = 4,4'-Biphenol bis(diphenyl phosphate)
\*\* TPP = (triphenyl phosphate)

TABLE IV

Flammability data for Injection molded FR-PS test pieces

| Exp No./ Formulation No. | Br-FR type | % Br-FR | % Br in formulation calculated | P-FR type | % P-FR | % P in formulation calculated | % Dicumyl in formulation | Color | Transparency | UL-94 |
|---|---|---|---|---|---|---|---|---|---|---|
| 1 | — | — | — | — | — | — | — | Colorless | Yes | Not rated |
| 2 | PBB-Br | 2.5 | 2.0 | — | — | — | — | Colorless | Yes | V-2 |
| 3 | PBB-Br | 1.8 | 1.5 | — | — | — | — | Colorless | Yes | V-2 |
| 4 | PBB-Br | 1.2 | 1.0 | — | — | — | — | Colorless | Yes | V-2 |
| 5 | PBB-Br | 1.8 | 1.5 | — | — | — | 0.2 | Colorless | Yes | V-2 |
| 6 | PBB-Br | 1.8 | 1.5 | — | — | — | 0.4 | Colorless | Yes | V-2 |
| 7 | PBB-Br | 1.8 | 1.5 | PFR-221 | 1.5 | 0.143 | — | Colorless | Yes | V-2 |
| 8 | PBB-Br | 1.8 | 1.5 | PFR-221 | 3.0 | 0.285 | — | Colorless | Yes | V-2 |
| 9 | PBB-Br | 1.8 | 1.5 | TPP | 1.5 | 0.143 | — | Colorless | Yes | V-2 |
| 10 | PBB-Br | 1.8 | 1.5 | TPP | 3.0 | 0.285 | — | Colorless | Yes | V-2 |
| 11 | PBB-Br | 1.8 | 1.5 | TPP | 0.8 | 0.076 | 0.1 | Colorless | Yes | V-2 |
| 12 | PBB-Br | 1.8 | 1.5 | TPP | 1.5 | 0.143 | 0.2 | Colorless | Yes | V-2 |

PFR-221 = 4,4'-Biphenol bis(diphenyl phosphate)
TPP = (triphenyl phosphate)

TABLE V

Test methods - Standard flammability test methods for injection molded and foamed flame-retarded polystyrene

| PROPERTY | METHOD | APPARATUS |
|---|---|---|
| LOI Limiting Oxygen Index | ASTM D 2863-77. Measuring the minimum oxygen concentration to support candle-like combustion of plastics. | Stanton Redcroft FTA Flammability Unit. |
| Flammability | DIN 4101-1 B-2, Fire behavior of building materials and elements Part 1 classification of building materials requirements and testing. | Hood and burner as specified by DIN |
| Flammability | UL-94V | Hood and burner as specified by UL |
| Compressive stress at 10% deflection | ASTM D1621, Compressive properties of rigid cellular plastic, procedure A. | Zwick 1435 material testing machine. |

The following Table VI discloses a number of injections molded PS formulations containing PBB-Br and other additives together with their respective LOI test results, UL-94 flammability rating, and color/transparency.

Table VI demonstrates the advantage of using high purity PBB-Br for obtaining excellent flame-retarding efficiency in styrene polymers. Formulation PF-13, which is used as a reference for all other formulations in Table VI, shows in itself a high LOI index. Incorporating different flame-retardants together with PBB-Br, while keeping a constant bromine content in all examples, results in LOI values comparable to that of the reference example.

In certain cases (see PF-16-20) the original amount of PBB-Br is maintained and the corresponding LOI values exceed that of the reference example.

All mixtures successfully pass transparency test, and almost all turn to be colorless. Selected examples are rated V-2 under UL-94 flammability testing.

All the above strongly points towards the advantage of using high purity PBB-Br as a flame-retardant in styrene polymers, where it enhances the flame-retarding efficiency when incorporated in different formulations together with brominated or other flame-retardants.

Example 8

Preparation of Polystyrene with PBB-Br for EPS

A typical laboratory set-up consisted of a four necked 0.5 L round-bottom flask, fitted with mechanical propeller stirrer, reflux condenser, thermometer and dropping funnel.

In the stirred flask were charged 100 ml deionized water, 0.01 g Polyvinyl alcohol (Mw $126 \times 10^3$) ex Aldrich dissolved in 10 ml deionized water, 0.025 g Dowfax 2A1, ex. Dow, an anionic surfactant, dissolved in 20 ml deionized water, 0.6 g $Ca_3(PO_4)_2$ ex Merck, which were heated to 90° C. Then a solution of 125 g styrene ex. Aldrich, 2.38 g PBB-Br ex. DSBG, 0.55 g Benzoyl Peroxide, ex. Fluka, was added into the flask from a dropping funnel over 3 hr. The mixture was stirred at 90° C. for 5.5 hr and then cooled to room temperature. Polystyrene beads were separated on a filter, washed on the filter with 200 ml of deionized water, then with 200 ml of methanol. The polymerization product was dried by vacuum.

Table VII herein below discloses flame-retarding test results of compression molded polystyrene formulation containing PBB-Br prepared from FR-PS produced as in Example 8. Flammability tests were carried out in accordance with the test methods detailed in Table V above.

70 g of FR-PS beads were compression molded at 180° C. for 2 minutes and cooled by water for 5 minutes. Test plates were cut from the molded article and tested for flammability by LOI and UL-94V methods. Results are shown in Table VII.

Because the polymerization process employed is known to be extremely sensitive to the presence of ionic species, low ionic bromide content PBB-Br, produced according to the present invention, was successfully employed. This results in a clear advantage in the final product. Preparation of a molded test piece from FR-polystyrene beads with PBB-Br is a simulative test for flammability of EPS foamed articles. The effectiveness of high purity PBB-Br is clearly seen in this process.

TABLE VI

Polystyrene formulations containing mixture of PBBBr (1.5% Br) + other additives – injection molded specimens

| | Formulation | | | | | | | | | | | |
|---|---|---|---|---|---|---|---|---|---|---|---|---|
| | PF-13 | PF-14 | PF-15 | PF-16 | PF-17 | PF-18 | PF-19 | PF-20 | PF-21 | PF-22 | PF-23 | PF-24 |
| PS Crystalline ex. DOW | 98.2 | 98.0 | 98.1 | 98.0 | 96.7 | 97.3 | 97.7 | 96.7 | 98.0 | 97.9 | 94.2 | 98 |
| PBBBr | 1.8 | 0.9 | 0.9 | 1.8 | 1.8 | 1.8 | 1.8 | 1.8 | 0.9 | 1.8 | 1.8 | 1.8 |
| FR-370[a] | | 1.1 | | | | | | | | | | |
| FR-513[b] | | | 1.0 | | | | | | | | | |
| FR-720[c] | | | | | | | | | 1.1 | | | |
| F-2200[d] | | | | | | | | | | 0.4 | | |
| CC-INITIATOR (DFB) | | | | 0.2 | | 0.1 | | | | | | |
| Reofos TPP (triphenyl phosphate) | | | | | 1.5 | 0.8 | | | | | | |
| NOR-116[f] | | | | | | | | 0.5 | | | | |
| Didodecyl 3,3'-thiodipropionate | | | | | | | | | | | 4 | |
| TAIC[e] | | | | | | | | | | | | 0.2 |
| PFR-221 | | | | | | | | 1.5 | | | | |
| Total % Br, calculated | 1.5 | 1.5 | 1.5 | 1.5 | 1.5 | 1.5 | 1.5 | 1.5 | 1.5 | 1.5 | 1.5 | 1.5 |
| LOI (% $O_2$) | 25.3 | 24.2 | 24.4 | 26.7 | 25.5 | 29.3 | 23.4 | 27.3 | 23.7 | 23.5 | 23.2 | 23.9 |
| Color/Appearance | colorless | colorless | colorless | colorless | colorless | colorless | light yellow | colorless | colorless | colorless | colorless | colorless |
| Transparent 3.2 mm | yes | Yes | yes | yes | yes | yes | yes | yes | yes | yes | yes | yes |
| UL-94 at 3.2 mm | V-2 | | | | | V-2 | | V-2 | | | | V-2 |

[a]FR-370 = Tris(tribromoneopentyl)phosphate, CAS Reg. Number 19186-97-1, ex DSBG.
[b]FR-513 = Tribromoneopentyl alcohol, CAS Reg. Number 36483-57-5, ex DSBG.
[c]FR-720 = Tetrabromobisphenol-A, bis(2,3-dibromopropylether), CAS Reg. Number 21850-44-2, ex DSBG.
[d]F-2200 = Brominated Epoxy Oligomer, CAS Reg. Number 68928-70-1, ex DSBG.
[e]TAIC = Tris-allyl iso cyanurate
[f]NOR-116 = ex. CIBA-GEIGY, CAS registry Number: 191680-81-6 100 (N,N"-1,2-ethanediylbis- reaction products with cyclohexane and peroxidized N-butyl-2,2,6,6-tetramethyl-4-piperidinamine-2,4,6-trichloro-1,3,5-triazine reaction products)

TABLE VII

| Flammability data for compression molded polystyrene beads | | |
| --- | --- | --- |
| Formulation P.S + PBB-Br prepared as in Example 8 | Unit | Value |
| % Br | % | 1.45 |
| LOI (% $O_2$) | % $O_2$ | 21.6 |
| UL-94 | Sec. | V-2 |

While examples of the invention have been described for purposes of illustration, it will be apparent that many modifications, variations and adaptations can be carried out by persons skilled in the art, without exceeding the scope of the claims.

The invention claimed is:

1. A one-pot process for the preparation of pentabromobenzyl bromide (PBB-Br), said process comprising the steps of:
   i) perbromination of toluene in a reaction mixture comprising dihalomethanes as solvent and $AlCl_3$ as catalyst:
   ii) deactivation of said catalyst by addition of water; and
   iii) benzylic bromination carried out in an organic solvent comprising dihalomethanes or a mixture of dihalomethanes, in the presence of water, and using 2,2'-azobisisobutyronitrile (AIBN) as an initiator, at a reaction temperature between about 45° C. and about 80° C.;
wherein said PBB-Br has a purity greater than 99.5% as defined by Gas Chromatography Analysis of PBB-Br, pentabromotoluene (5-BT) and residual solvents.

2. A highly pure PBB-Br prepared according to the process of claim 1, exhibiting a purity greater than 99.5%, as defined by Gas Chromatography Analysis of PBB-Br, pentabromotoluene (5-UT) and residual solvents.

3. The highly pure PBB-Br of claim 2, further exhibiting a thermal stability of more than 250° C. when characterized by Thermogravimetric Analysis at a temperature of 10% weight loss, an ionic bromide content of 20 ppm or less, and an APHA value approximately 15 or less.

4. Method of flame-retarding an Expanded Polystyrene Foam (EPS), said method comprising adding to said EPS a flame-retarding effective amount of the highly pure PBB-Br of claim 2.

5. Flame-retarded Expanded Polystyrene Foam (EPS) comprising a flame-retarding effective amount of the highly pure PBB-Br of claim 2.

6. Method of flame-retarding a transparent polystyrene, said method comprising adding to said transparent polystyrene a flame-retarding effective amount of the highly pure PBB-Br of claim 2.

7. Transparent flame-retarded polystyrene comprising a flame-retarding effective amount of the highly pure PBB-Br of claim 2.

8. Transparent flame-retarded polystyrene according to claim 7, further comprising other flame-retarding additives.

9. Transparent flame-retarded polystyrene according to claim 8, wherein said additives are selected from the group consisting of tris(tribromoneopentyl)phosphate, tribromoneopentyl alcohol, tetrabromobisphenol-A, bis(2,3-dibromopropylether), brominated epoxy oligomer, tris-allyl iso cyanurate, 1,3-propanediamine, N,N"-1,2-ethanediylbis-reaction products with cyclohexane and peroxidized N-butyl-2,2,6,6-tetramethyl-4-piperidinamine-2,4,6-trichloro-1,3,5-triazine reaction products, 4,4'-biphenol bis(diphenyl phosphate), didodecyl 3,3'-thiodipropionate, triphenyl phosphate, 2,3-dimethyl-2,3-diphenyl butane, and mixtures thereof.

10. Method for rendering flammable polystyrene flame retarded and UL94 V-2 rated, comprising adding to said polystyrene a flame-retarding effective amount of the highly pure PBB-Br of claim 2.

11. V-2 rated polystyrene comprising a flame-retarding effective amount of the highly pure PBB-Br of claim 2.

12. V-2 rated polystyrene according to claim 11, further comprising other flame-retarding additives.

13. V-2 rated polystyrene according to claim 12, wherein said additives are selected from the group consisting of tris (tribromoneopentyl)phosphate, tribromoneopentyl alcohol, tetrabromobisphenol-A, bis(2,3-dibromopropylether), brominated epoxy oligomer, tris-allyl iso cyanurate, 1,3-propanediamine, N,N'-1,2-ethanediylbis-reaction products with cyclohexane and peroxidized N-butyl-2,2,6,6-tetramethyl-4-piperidinamine-2,4,6-trichloro-1,3,5-triazine reaction products, 4,4'-biphenol bis(diphenyl phosphate), didodecyl 3,3'-thiodipropionate, triphenyl phosphate, 2,3-dimethyl-2,3-diphenyl butane, and mixtures thereof.

* * * * *